US 8,742,102 B2

United States Patent
Helmreich et al.

(10) Patent No.: US 8,742,102 B2
(45) Date of Patent: Jun. 3, 2014

(54) PROCESS FOR ENANTIOMERIC SEPARATION OF RACEMIC DIHYDRO-1,3,5 TRIAZINES VIA PREFERENTIAL CRYSTALLIZATION

(75) Inventors: Matthias Helmreich, Heidelberg (DE); Claus-Peter Niesert, Seehelm-Jugenheim (DE); Daniel Cravo, Montesson (FR); Gérard Coquerel, Boos (FR); Guillaume Levilain, Deville les Rouen (FR); Saoussen Wacharine-Antar, Menzel Bouzelfa (TN); Pascal Cardinael, Isneauville (FR)

(73) Assignee: Poxel, Lyon (FR)

( * ) Notice: Subject to any disclaimer, the term of this patent is extended or adjusted under 35 U.S.C. 154(b) by 248 days.

(21) Appl. No.: 13/138,728

(22) PCT Filed: Mar. 26, 2010

(86) PCT No.: PCT/EP2010/054037
§ 371 (c)(1),
(2), (4) Date: Dec. 7, 2011

(87) PCT Pub. No.: WO2010/109015
PCT Pub. Date: Sep. 30, 2010

(65) Prior Publication Data
US 2012/0071655 A1    Mar. 22, 2012

(30) Foreign Application Priority Data
Mar. 26, 2009  (EP) .................................. 09004315

(51) Int. Cl.
*C07D 251/10* (2006.01)
*A61K 31/53* (2006.01)
*A61P 3/04* (2006.01)

(52) U.S. Cl.
USPC ............ 544/204; 544/206; 544/208; 544/209

(58) Field of Classification Search
USPC .................. 544/204, 206, 208, 209
See application file for complete search history.

(56) References Cited

U.S. PATENT DOCUMENTS 6,022,409 A    2/2000  Coquerel et al.
7,501,511 B2 *  3/2009  Moinet et al. ................. 544/206
2006/0223803 A1   10/2006  Moinet et al.

FOREIGN PATENT DOCUMENTS

WO    WO 95/08522     3/1995
WO    WO 2004/089917  10/2004
WO    WO 2010/012746   2/2010

OTHER PUBLICATIONS

International Search Report for PCT/EP2010/054037, mailed Jun. 10, 2010.
Written Opinion of the International Searching Authority for PCT/EP2010/054037, mailed Jun. 10, 2010.
Coquerel, G., "Preferential Crystallization", Topics in Current Chemistry, vol. 269, (Jan. 1, 2007), pp. 1-51.

* cited by examiner

*Primary Examiner* — Venkataraman Balasubramanian
(74) *Attorney, Agent, or Firm* — Nixon & Vanderhye P.C.

(57) ABSTRACT

A new process for the enantiomeric separation of racemic 3,6-dihydro-1,3,5-triazine derivatives for the treatment of disorders associated with insulin-resistance syndrome, by preferential crystallization.

13 Claims, 4 Drawing Sheets

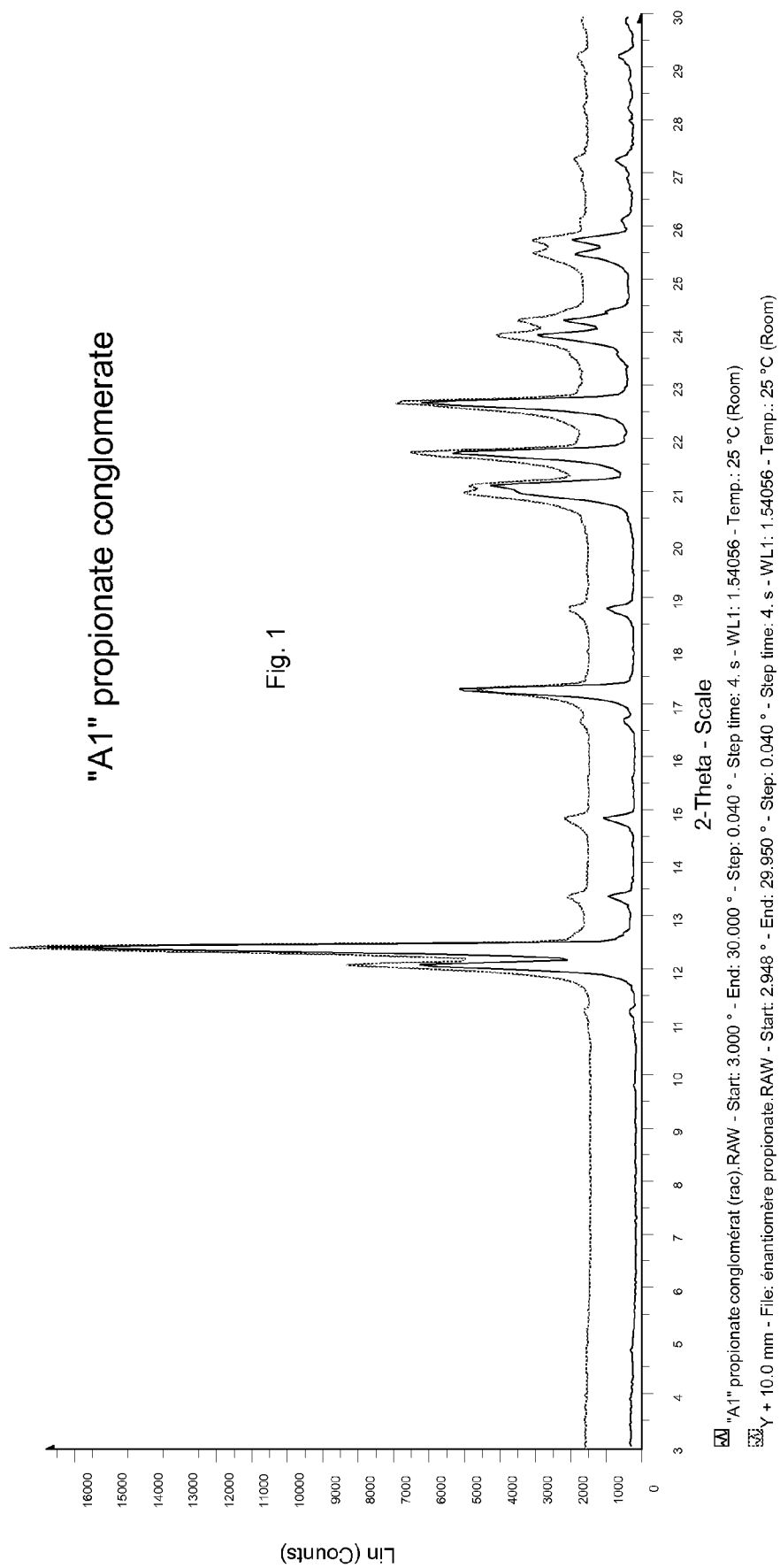

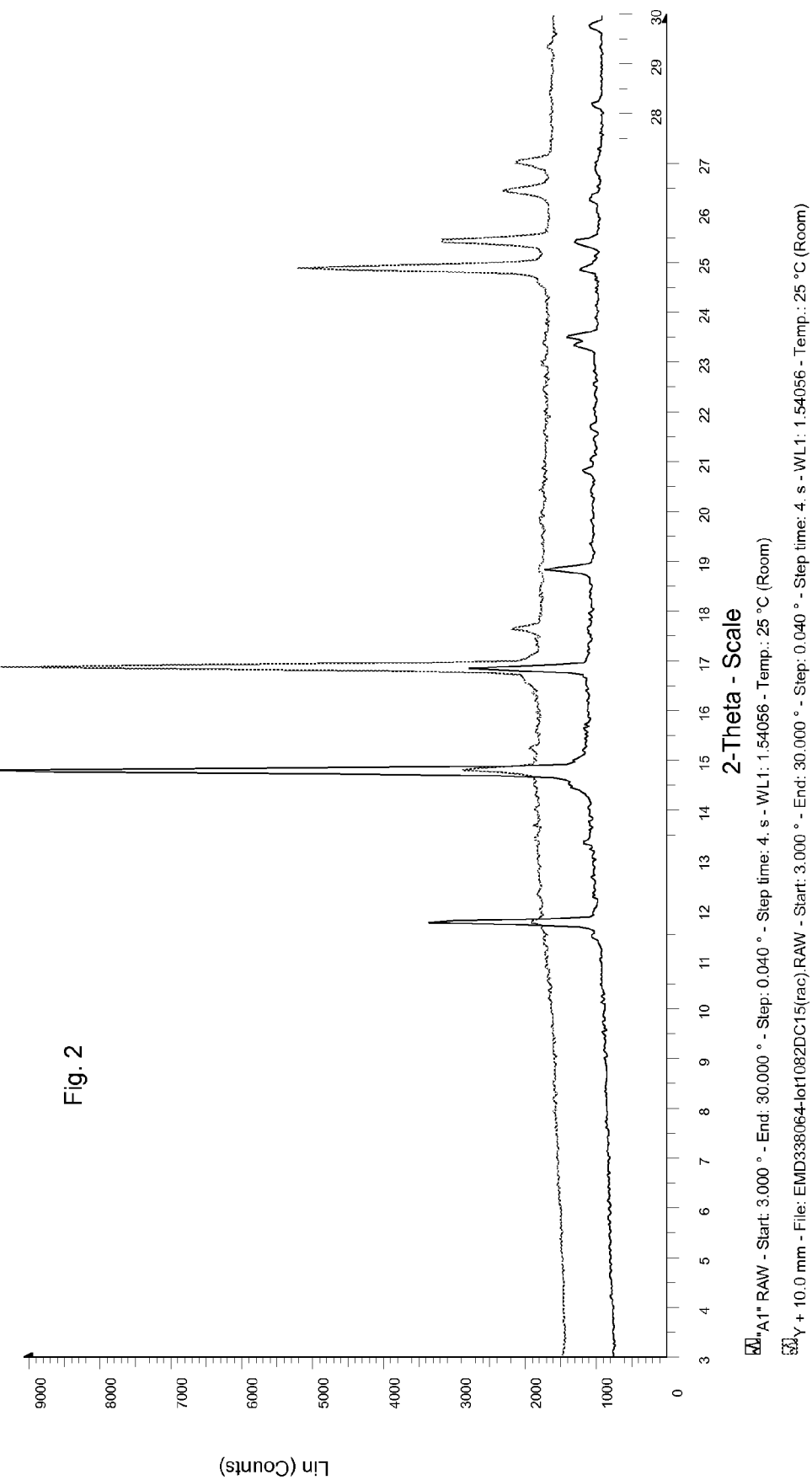

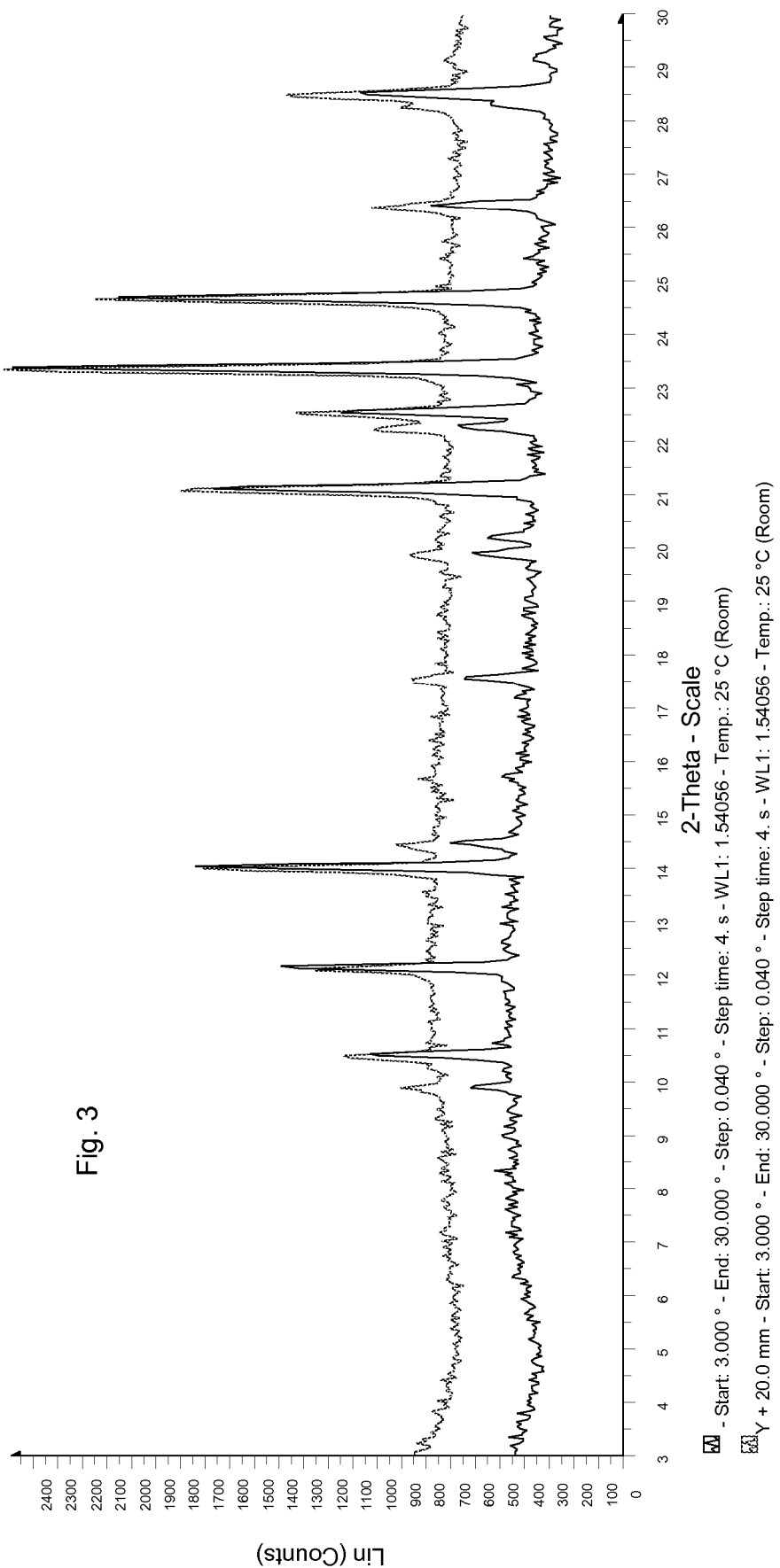

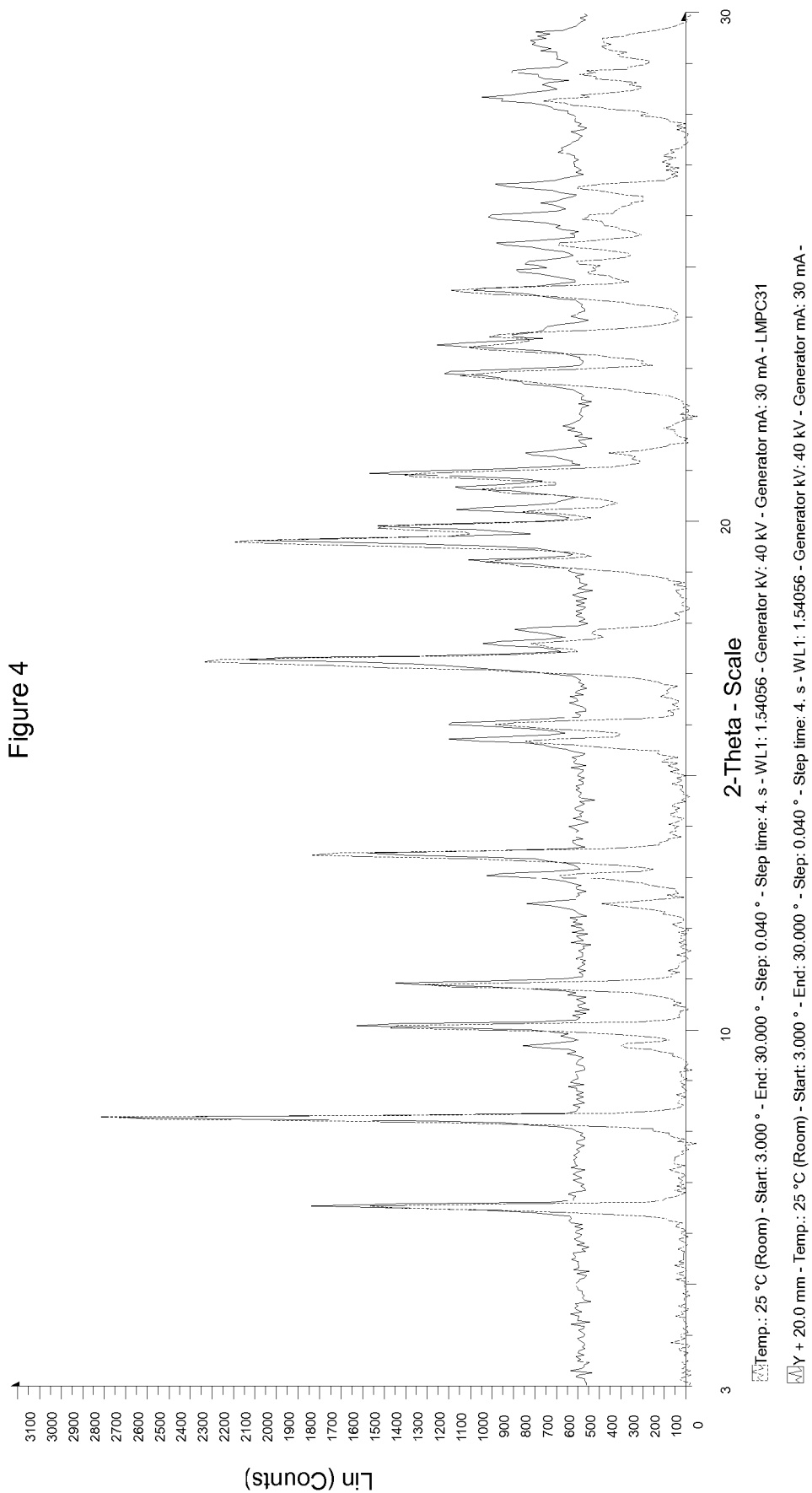

PROCESS FOR ENANTIOMERIC SEPARATION OF RACEMIC DIHYDRO-1,3,5 TRIAZINES VIA PREFERENTIAL CRYSTALLIZATION

This application is the U.S. national phase of International Application No. PCT/EP2010/054037, filed 26 Mar. 2010, which designated the U.S., and claims priority to EP Application No. 09004315.9, filed 26 Mar. 2009, the entire contents of which is hereby incorporated by reference.

3,6-Dihydro-1,3,5-triazine derivatives show pharmacological properties in the treatment of pathological conditions associated with the insulin-resistance syndrome. Several patents describe the preparation of 3,6-dihydro-1,3,5-triazine derivatives. For example, in U.S. Pat. No. 3,287,366 the synthesis of dihydro-triazine bearing the following structure is described:

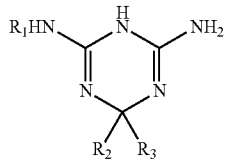

The synthesis involves the reaction of a mono-substituted bisguanidine and an aldehyde or ketone in presence of an acid at elevated temperatures.

Patent JP48064088 describes the synthesis of dihydro-triazines bearing the following structure:

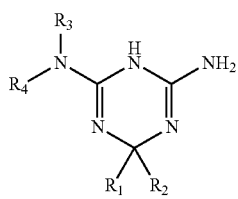

The analogous synthesis also involves heating under acidic conditions.

Patent JP54014986 describes the synthesis of dihydro-triazines bearing the following structure:

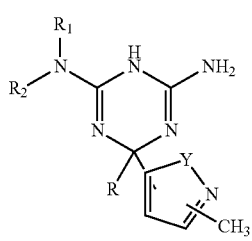

Similarly, this method requires heating under acidic conditions.

Patent application WO 01/55122 describes the synthesis of dihydro-triazines of the following structure:

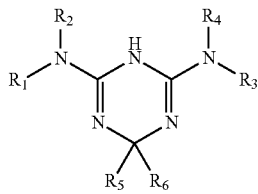

The synthesis is directed to the reaction of mono-substituted bisguanidines and an acetal, hemiacetal, ketal, hemiketal, aldehyde, or ketone in presence of an acid at elevated temperatures.

WO 04/089917 discloses a process for the separation of enantiomeric mixtures of dihydro-1,3,5 triazines by using a chiral resolving agent (diastereomeric resolution). This method yields a product exhibiting an ee (enantiomeric excess) of 70% (enantiomeric purity 85%).

WO 95/08522 or U.S. Pat. No. 6,022,409 discloses a method of optical enantiomer resolution by preferential crystallization.

G. Coquerel published an article "Preferential Crystallization" in Top Curr Chem (2007) 269: 1-51; © Springer-Verlag Berlin Heidelberg 2007; published online: 4 Nov. 2006.

The article focuses primarily on chiral discrimination in the solid state, i.e. the formation of conglomerates, how to detect them and the various benefits that can be retrieved from chiral recognition in crystal lattices.

Preferential crystallization is applicable to racemic mixtures which crystallize as a stable conglomerate. Statistics show that approximately 5% of racemic mixtures form a stable conglomerate. The advantages of this method are the following:

theoretical quantitative yield as the mother liquors can be recycled;

no need for a resolving agent (which is expensive in most cases).

A conglomerate is a mixture of mirror-image crystallized phases exhibiting symmetrical enantiomeric excesses.

The invention had the object of finding a new method for the resolution of the two optical enantiomers of dihydro-1,3,5 triazines of formula I.

This would save energy, reduce the amount of generated waste and improve the safety of the process.

Unexpectedly, it has been found that compounds of formula I can form stable conglomerate salts and that the optical enantiomers of these salts can be resolved by preferential crystallization.

The advantages of this method are theoretical quantitative yield as the mother liquors can be recycled, no need for a chiral resolving agent, which is expensive in most cases.

The invention relates to a process for the resolution of the two optical enantiomers of a salt of compounds of the formula I or a solvate of this salt

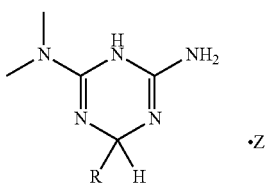

in which
R is methyl, phenyl, 4-hydroxy-phenyl or 4-methoxyphenyl,
Z is hydrochloric acid, hydrobromic acid, nitric acid, acetic acid, propanoic acid, 2,4-dichlorophenylacetic acid, 3,4-dichlorophenyl acetic acid, barbituric acid, chloroacetic acid, adipic acid, glycolic acid, succinic acid, or (±)di-O, O'-p-tolyltartaric acid,
or a tautomer thereof,
by preferential crystallization.

Formula I also embraces the tautomeric forms of the compounds.

For instance, tautomeric forms of the compound of formula I in which R is methyl include the following:

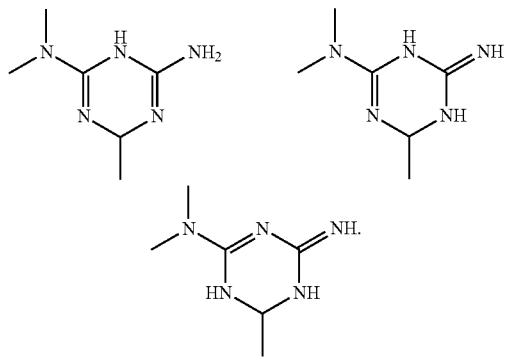

The salts of compounds of formula I can be formed with different ratios Z: compound of formula I. For instance, the salts can be mono-, di- or tri-salts, i.e. 1, 2 or 3 molecules of Z respectively for one molecule of formula I. Another example would be that of a salt with 1, 2 or 3 molecules of formula I for one molecule of Z.

Preferably, the separation of the enantiomers is directed to a process, wherein
    a) a racemic mixture of a salt of a compound of formula I

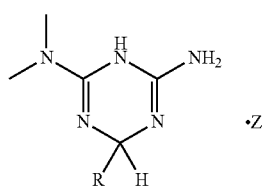

in which
R is methyl, phenyl, 4-hydroxy-phenyl or 4-methoxyphenyl,
Z is hydrochloric acid, hydrobromic acid, nitric acid, acetic acid, propanoic acid, 2,4-dichlorophenylacetic acid, 3,4-dichlorophenyl acetic acid, barbituric acid, chloroacetic acid, adipic acid, glycolic acid, succinic acid or (±)di-O, O'-p-tolyltartaric acid,
is dissolved in an organic solvent,
    b) the solution is seeded with a single enantiomer of the salt of the compound of formula I,
    c) the obtained crystallized enantiomer is isolated.

The racemic mixture used in step (a) is a racemic mixture that crystallizes as a conglomerate.

A preferred process for the resolution of the two optical enantiomers corresponds to compounds of formula I in which R is methyl or 4-hydroxyphenyl; most preferably R is methyl.

Preferably, Z is hydrochloric acid, propanoic acid, adipic acid, chloroacetic acid, glycolic acid, hydrobromic acid or succinic acid.

Preferably, Z is propanoic acid, also named propionic acid.

Preferably, the process is performed in toluene, acetone, ethanol, isopropanol, methanol, water or mixtures of these solvents.

Preferably, the process is performed in an organic solvent selected in the group consisting of ethanol, isopropanol, methanol and mixtures thereof. Most preferably, ethanol is used as the organic solvent.

According to a particular embodiment, the process is carried out with a co-solvent, in particular methanol.

Physical conditions of the process, including temperatures and kinetic schedule, are readily determined by one of ordinary skill in the art depending on the chosen salt and solvent.

Preferably, the process is performed at temperatures between −20 and 90° C., most preferably between 0 and 65° C., highly preferred between 0 and 50° C.

A highly preferred process is the one wherein:
    a) a suspension of a racemic mixture 2-amino-3,6-dihydro-4-dimethylamino-6-methyl-1,3,5-triazine ("A1") propionate in ethanol is heated at 40-50° C. until a clear solution is obtained,
    b) the solution is cooled and seeded with a single enantiomer of the 2-amino-3,6-dihydro-4-dimethylamino-6-methyl-1,3,5-triazine propionate (more particularly R-enantiomer),
    c) at temperatures between 5 and 10° C. the crystallized 2-amino-3,6-dihydro-4-dimethylamino-6-methyl-1,3,5-triazine propionate (more particularly R-enantiomer) is isolated.

The process according to the invention is preferably carried out repetitively. More specifically, after step c), the same racemic mixture of step a) is added to the mother liquor (solution recovered after harvesting the crystals—step c)), preferably the amount by weight of the added racemic mixture is equal to the amount by weight of the harvested (or isolated) crystals. Said mother liquor presents consequently an excess of the other (or opposite) enantiomer. According to a specific embodiment, the obtained solution is then seeded with the other enantiomer. The other crystallized enantiomer can thereafter be isolated. The cycle of operations (or steps) can then be repeated accordingly (1, 2, 3, 4, 5 times or more) to separate the first and second enantiomers of the racemic mixture successively.

According to a particular embodiment, the process comprises, after steps a, b and c the following steps:
    d) the same racemic mixture of step a) (or subsequently the same racemic mixture of previous step d) is added to the solution recovered after step c) (or subsequently the solution recovered of previous step f), preferably the amount by weight of the added racemic mixture is equal to the amount by weight of the previously isolated crystals,
    e) optionally the obtained solution is then seeded with the other enantiomer,
    f) the other crystallized is isolated.

Advantageously, steps d), e) and f) are repeated to separate the first and second enantiomers of the racemic mixture successively.

Conglomerates can be characterized by using X-ray analysis and the enantiomeric excess (ee) can be determined by HPLC.

Once a conglomerate is identified, the racemic-acid salt is synthesized and the process of preferential crystallization is performed. The pure isolated enantiomer is then turned into to the right salt form (if necessary).

A couple of enantiomers can crystallize in three major ways:
the conglomerate;
the racemic mixture; the substance forms a single crystalline phase in which the two enantiomers are present in an ordered 1:1 ratio in the unit-cell;
complete solid solution; wherein the two enantiomers coexist in an unordered manner in the crystal lattice.

A conglomerate is a mechanical mixture of enantiomerically pure crystals (the absence of partial solid solution is supposed). The space group of any pure enantiomer is chiral. They exhibit the same XRPD (X-Ray Powder Diffraction) patterns. Statistics show that 5-10% of the couples of enantiomers crystallize as a conglomerate.

In this case, pure enantiomers can be easily isolated from the racemic mixture by crystallization. When the enantiomers cannot be heated (problem of degradation), the addition of another component (preferably a solvent) allows the enantiomer in excess to be separated.

Preferential crystallization can be implemented to the racemic mixtures of the present invention because the couples of enantiomers of said mixtures crystallize as conglomerates.

The racemic mixtures of the selected salts of the invention crystallize as conglomerates. One of ordinary skill in the art will know the classical procedures to produce the selected salts of the invention.

The preferential crystallization method, as disclosed in WO95/08522, more specifically involves entering, each time crystallization starts, the two-phase domain containing excess enantiomer and the saturated solution (obtained after seeding), and cooling according to a kinetic schedule (which can be readily defined by one of ordinary skill in the art based on physicochemical parameters, including given solvent, concentrations, and salt). Cooling makes the enantiomer crystallize, which can thus be isolated. A racemic mixture (advantageously of fine particle size) is preferably added to the mother liquors obtained after harvesting the crystals, the mother liquors then being advantageously heated, more specifically to a temperature lower than that of homogenization of the solution so that excess enantiomer is present only in a solid state in equilibrium with the solution. Further cooling, and preferably seeding with the other enantiomer, produces the other enantiomer and completes the cycle of operations which may then be carried out repetitively.

The preferential crystallization is consequently an attractive method for the separation of enantiomers. The starting situation is composed of a mixture of enantiomers enriched in one optical isomer. When the AS3PC (autoseeded polythermic programmed preferential crystallization) method is applied, a part of the enantiomer in excess is solid at the starting point (i.e. at the highest temperature). By contrast, for the S3PC method, (Seeded polythermic programmed preferential crystallization), the initial enrichment is completely dissolved (the starting situation is a homogeneous solution). Then, a small amount of pure enantiomer (of the same chirality as that of the initial excess) is added to seed the system. The supersaturation is created and increased by the application of a cooling ramp (according to a kinetic schedule). The crystallization of the enantiomer initially in excess is due to a stereoselective secondary nucleation and the crystal growth. If the process is correctly optimized, the germination of the opposite enantiomer does not occur before the end of the process (filtration). When the maximal quantity of isomer has crystallized (the mother liquor has reached a point close to the metastable solubility of the crystallizing enantiomer), a swift filtration is implemented. Ideally, the pure optical isomer and a liquid enriched in the opposite enantiomer are obtained. Then, an equal mass of racemic mixture as the one collected by filtration is added to the mother liquor and the temperature is increased up to the complete dissolution of the solid. On cooling, the supersaturated solution is seeded by the second enantiomer leading to the preferential crystallization of this second enantiomer. The following steps consist in repeating these alternate preferential crystallizations (R, S, R, S, R, S, R, S . . . or vice-versa).

Other aspects and advantages of the present invention are illustrated by the following examples which must be considered as illustrative and not restrictive.

BRIEF DESCRIPTION OF THE FIGURES

FIG. 1: XRPD analysis of the 2-amino-3,6-dihydro-4-dimethylamino-6-methyl-1,3,5-triazine propionate conglomerate (lower spectrum) compared to the XRPD analysis of a single enantiomer (upper spectrum).

FIG. 2: XRPD analysis of the 2-amino-3,6-dihydro-4-dimethylamino-6-methyl-1,3,5-triazine hydrochloride conglomerate (lower spectrum) compared to the XRPD analysis of a single enantiomer (upper spectrum).

FIG. 3: XRPD analysis of the 2-amino-3,6-dihydro-4-dimethylamino-6-methyl-1,3,5-triazine 2,4dichlorophenylacetate (methanol solvate) conglomerate (lower spectrum) compared to the XRPD analysis of a single enantiomer (upper spectrum).

FIG. 4: XRPD analysis of the 2-amino-3,6-dihydro-4-dimethylamino-6-methyl-1,3,5-triazine (±)di-O,O'-p-tolyltartrate conglomerate (lower spectrum) compared to the XRPD analysis of a single enantiomer (upper spectrum).

To prove that a salt crystallizes as a conglomerate, several experiments were performed.

To prove definitely that a conglomerate exists, both enantiomer and racemic mixture are crystallized using the same protocol. Then, both solids are analysed by XRPD. If the patterns match, the salt crystallizes as a conglomerate.

EXAMPLES

I. General Procedure for Characterization Experiments of Six Conglomerate Salts

This procedure was used to screen the potential interest of specific conglomerates of the invention.

Procedure: A starting base solution of 62.9% ee of 2-amino-3,6-dihydro-4-dimethylamino-6-methyl-1,3,5-triazine is prepared from a mixture of enantiomeric hydrochloride salts. The concentration is determined by HPLC using an external standard. The acids (3.22 mmol for 1:1 salts, 1.61 mmol for 2:1 salts) are charged to a Radleys parallel reaction carousel workstation tube. EtOH/i-PrOH (6 ml) is added and the acid stirred. The appropriate amount of base solution (62.9% ee, 3.22 mmol) is added and the resulting mixtures are stirred for 15 mins. The tubes are evacuated to remove all solvent. The salts are then dissolved in the minimum amount of solvent (ethanol or IPA as given below) required for dissolution at reflux temperature. The solvent is added in 0.25 ml portions until complete dissolution at 80° C. These are allowed to cool to 21° C. overnight. This is then repeated for each acid using 2× and 3× the solvent amount. The reactions are analyzed by HPLC of liquors and crystals after filtration (no wash).

After determination of the necessary solvent amount to dissolve 3.22 mmol salt, two more experiments are carried out on each salt using 1.5 times and ⅔ times the solvent amount. The crystals in this case are pressed dry and also washed and dried.

Results of experiments with 62.9% ee starting base:

| acid | Just dissolved hot | 2/3 times solvent amount | 1.5 times solvent amount |
|---|---|---|---|
| Propionic acid | (a): 3.7% ee (R) <br> (b): 84.8% ee (R) <br> (c): 4.9% ee (R) <br> (d): 87.8% ee (R) <br> i-PrOH (4.85 ml) | (a): 10.3% ee (R) <br> (b): 90.0% ee (R) <br> (c): 15.0% ee (R) <br> (d): 96.4% ee (R) | (a): 28.7% ee (R) <br> (b): 92.9% ee (R) <br> (c): 31.5% ee (R) <br> (d): 96.9% ee (R) |
| 2:1 Adipic acid | (a): 42.9% ee (R) <br> (b): 71.9% ee (R) <br> (c): 44.3% ee (R) <br> (d): 72.7% ee (R) <br> EtOH (25 ml) | (a): 49.3% ee (R) <br> (b): 65.4% ee (R) <br> (c): 51.2% ee (R) <br> (d): 66.9% ee (R) | (a): 50.2% ee (R) <br> (b): 64.6% ee (R) <br> (c): 53.1% ee (R) <br> (d): 65.7% ee (R) |
| Chloroacetic acid | (a): 44.3% ee (R) <br> (b): 88.4% ee (R) <br> (c): 46.0% ee (R) <br> (d): 87.9% ee (R) <br> EtOH (1.5 ml) | (a): 47.8% ee (R) <br> (b): 86.2% ee (R) <br> (c): 49.1% ee (R) <br> (d): 91.1% ee (R) | (a): 45.4% ee (R) <br> (b): 90.0% ee (R) <br> (c): 47.0% ee (R) <br> (d): 96.1% ee (R) |
| Glycolic acid | (a): 15.7% ee (R) <br> (b): 65.4% ee (R) <br> (c): 19.4% ee (R) <br> (d): 69.3% ee (R) <br> EtOH (1.25 ml) | (a): 16.9% ee (R) <br> (b): 63.4% ee (R) <br> (c): 36.5% ee (R) <br> (d): 70.1% ee (R) | (a): 16.5% ee (R) <br> (b): 74.2% ee (R) <br> (c): 23.0% ee (R) <br> (d): 76.0% ee (R) |
| HBr | (a): 1.5% ee (R) <br> (b): 69.1% ee (R) <br> (c): 6.5% ee (R) <br> (d): 70.6% ee (R) <br> EtOH (2.75 ml) | (a): −2.6% ee (R) <br> (b): 68.6% ee (R) <br> (c): 10.1% ee (R) <br> (d): 70.2% ee (R) | (a): 8.0% ee (R) <br> (b): 71.6% ee (R) <br> (c): 26.3% ee (R) <br> (d): 73.1% ee (R) |
| Succinic acid (1:1) | (a): 54.7% ee (R) <br> (b): 56.9% ee (R) <br> (c): 56.3% ee (R) <br> (d): 56.7% ee (R) <br> EtOH (9.5 ml) | (a): 54.8% ee (R) <br> (b): 53.8% ee (R) <br> (c): 57.6% ee (R) <br> (d): 58.1% ee (R) | (a): 54.6% ee (R) <br> (b): 55.0% ee (R) <br> (c): 52.6% ee (R) <br> (d): 56.1% ee (R) | abbreviations:
liquor before wash: (a)
crystals pressed dry: (b)
liquor + wash: (c)
crystals washed: (d)

Under such experimental conditions, this table shows that 2-amino-3,6-dihydro-4-dimethylamino-6-methyl-1,3,5-triazine, propionic acid salt corresponds to the optimal salt to be resolved by preferential crystallization.

II. Entrainment of "A1" HCl Salt

A saturated solution of racemic HCl salt is prepared by heating 50 g of salt in EtOH (350 ml) to reflux. A clear solution is formed. This is allowed to cool to 40° C. The mixture is seeded with a slurry of racemic HCl salt.

Crystallization is observed. This is allowed to equilibrate overnight. The mixture is filtered into the reaction vessel (preheated to 40° C.). This is heated to 60° C. to ensure complete dissolution, cooled to 40° C. and sampled to determine the concentration by HPLC. This is then cooled to 13° C. in increments of 1° C./5 min. At 13° C. a small amount of crystallisation is observed. A seed sample is also added and this is allowed to equilibrate overnight. A sample is removed for concentration determination at 13° C.

The mixture is heated to 60° C. to dissolve in EtOH all solid. This is then cooled to 40° C. and held at this temperature for 30 min. A freshly sonicated slurry of 94.5% ee (R)-hydrochloride salt (4.8 g in 25 ml) is added and the reaction temperature is decreased by 1° C. every 5 min. The mixture is sampled every 10 min to determine optical purity of the crystals. The results are noted below.

Concentration of sat. solution at 40° C.=92.2 g/L
Concentration at 13° C.=69.74 g/L

| Time (min) | Internal temperature (° C.) | % S (ML*) | % R (ML) | ee (S) ML | % R Crystals | % S Crystals | ee (R) Crystals |
|---|---|---|---|---|---|---|---|
| 0 | 40 | 49.47 | 50.53 | −1.1 | — | — | — |
| 10 | 38.5 | 49.6 | 50.4 | −0.8 | — | — | — |
| 20 | 37 | 49.89 | 50.11 | −0.2 | — | — | — |
| 30 | 35 | 49.81 | 50.19 | −0.4 | 95.46 | 4.54 | 90.9 |
| 40 | 33 | 50.19 | 49.81 | 0.4 | — | — | — |
| 50 | 31 | 50.58 | 49.42 | 1.2 | — | — | — |
| 60 | 29 | 50.82 | 49.18 | 1.6 | 94.81 | 5.19 | 89.6 |
| 70 | 27 | 51.62 | 48.38 | 3.2 | — | — | — |
| 80 | 25 | 52.02 | 47.98 | 4.0 | — | — | — |
| 90 | 23 | 52.44 | 47.56 | 4.9 | 81.79 | 17.63 | 64.1 |
| 100 | 22 | 52.4 | 47.60 | 4.8 | — | — | — |
| 110 | 19.5 | 51.87 | 48.13 | 3.7 | — | — | — |
| 120 | 17.5 | 51.10 | 48.90 | 2.2 | 70.36 | 29.64 | 40.7 |
| 130 | 15.5 | 51.01 | 48.98 | 2.0 | — | — | — |
| 140 | 13.0 | 50.31 | 49.69 | 0.6 | — | — | — |

*ML = mother liquor

This table shows that harvesting crystals should be implemented for a racemic mixture of 2-amino-3,6-dihydro-4-dimethylamino-6-methyl-1,3,5-triazine ("A1"). HCl within 30 minutes to give the best resolution with respect to a decrease of temperature by 1° C. every 5 minutes.

III. Enantiomeric Separation from "A1" Propionate Salt

A suspension of a racemic mixture of 200 g of 2-amino-3,6-dihydro-4-dimethylamino-6-methyl-1,3,5-triazine ("A1") propionate in 600 g of ethanol is heated until a clear solution is obtained (45° C.). This solution is then cooled and seeded with a single enantiomer of the 2-amino-3,6-dihydro-4-dimethylamino-6-methyl-1,3,5-triazine propionate (R-enantiomer) and only the seeded isomer starts to crystallize. After reaching the final temperature (7° C.) the crystals are isolated (40 g; 76-80% ee of the R-enantiomer) and the mother liquor is collected. The progress of the crystallization can be monitored via online polarimetry of the liquors. By applying this method it is possible to find the optimal point (in terms of Enantiomeric purity and yield) for the isolation of the crystals. For the next cycle, 40 g of racemic 2-amino-3,6-dihydro-4-dimethylamino-6-methyl-1,3,5-triazine propionate are added to the mother liquor of the first cycle and the suspension is heated in order to get a clear solution with the initial concentration. This solution (now enriched with the S-enantiomer) is cooled down and seeded with crystals of the S-enantiomer. The crystals are isolated again at the final temperature (40 g; 76-80% ee S-enantiomer) and the mother liquor is collected (now enriched with the R-enantiomer).

This cycle can be repeated several times without a major decrease of the enantiomeric excess nor the yield.

HPLC-method for determination of enantiomeric excess:
HPLC-system: Merck Hitachi LaChrom
Stationary phase: Chirobiotic™ T2
Mobile phase: methanol with 0,1% w/w Ammonium Trifluoroacetate
Flow rate: 1 ml/minute
Column temperature: 25° C.
Injection volume: 50 ul
Pressure: 50-200 bar
UV detection at 240 nm

The invention claimed is:
1. A process for the resolution of the two optical enantiomers of a salt of a compound of formula I

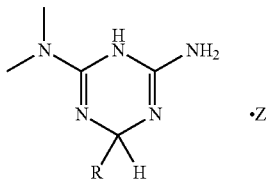

in which
R is methyl, phenyl, 4-hydroxy-phenyl or 4-methoxyphenyl,
Z is propanoic acid or 2,4-dichlorophenylacetic acid,
or a tautomer thereof, by preferential crystallization.

2. The process according to claim 1, wherein it comprises the following steps:
a) a racemic mixture of a salt of a compound of formula (I)

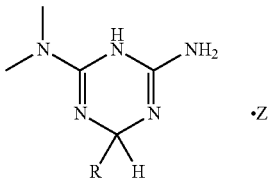

in which
R is methyl, phenyl, 4-hydroxy-phenyl or 4-methoxyphenyl,
Z is propanoic acid or 2,4-dichlorophenylacetic acid,
is dissolved in an organic solvent,
b) the solution is seeded with a single enantiomer of the salt of the compound of formula I,
c) the obtained crystallized enantiomer is isolated.

3. The process according to claim 1, wherein R is methyl or 4-hydroxyphenyl.
4. The process according to claim 1, wherein R is methyl.
5. The process according to claim 1, in which Z is propanoic acid.
6. The process according to claim 1, wherein the process is performed in a solvent selected from the group consisting of ethanol, isopropanol, methanol and mixtures thereof.
7. The process according to claim 1, wherein the process is performed at temperatures between −20 and 90° C.
8. The process according to claim 1, wherein:
a) a suspension of a racemic mixture 2-amino-3,6-dihydro-4-dimethylamino-6-methyl-1,3,5-triazine ("A1") propionate in ethanol is heated at 40-50° C. until a clear solution is obtained,
b) the solution is cooled and seeded with a single enantiomer of the 2-amino-3,6-dihydro-4-dimethylamino-6-methyl-1,3,5-triazine propionate,
c) at temperatures between 5 and 10° C. the crystallized 2-amino-3,6-dihydro-4-dimethylamino-6-methyl-1,3,5-triazine propionate is isolated.

9. The process according to claim 2, wherein it further comprises the following steps:
d), after step c), the same racemic mixture of step a) is added to the solution recovered after step c),
e) optionally the obtained solution is then seeded with the other enantiomer,
f) the other crystallized enantiomer is isolated.

10. The process according to claim 9, wherein steps d), e) and f) are repeated to separate the first and second enantiomers of the racemic mixture successively.

11. The process according to claim 7, wherein the process is performed at temperatures between 0 and 50° C.

12. The process according to claim 8, wherein 2-amino-3,6-dihydro-4-dimethylamino-6-methyl-1,3,5-triazine propionate is (R)-2-amino-3,6-dihydro-4-dimethylamino-6-methyl-1,3,5-triazine propionate.

13. The process according to claim 9, wherein the amount by weight of the added racemic mixture is equal to the amount by weight of the isolated crystals.

* * * * *